US00PP33297P2

(12) United States Plant Patent
Hansen

(10) Patent No.: US PP33,297 P2
(45) Date of Patent: Jul. 27, 2021

(54) ***HOSTA* PLANT NAMED 'TEARS IN HEAVEN'**

(50) Latin Name: ***Hosta* hybrid (Tratt.)**
Varietal Denomination: Tears in Heaven

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 16/974,298

(22) Filed: Dec. 18, 2020

(51) Int. Cl.
*A01H 5/12* (2018.01)
*A01H 6/12* (2018.01)

(52) U.S. Cl.
USPC ..... Plt./353

(58) Field of Classification Search
USPC ..... Plt./353
See application file for complete search history.

(56) References Cited

PUBLICATIONS http://www.plantsgalore.com/Hostas/cultivars/t/Hosta_Tears_in_Heaven.htm Retrieved from the Internet on Mar. 30, 2021 (3 pages total).*

* cited by examiner

*Primary Examiner* — Susan McCormick Ewoldt

(57) ABSTRACT

A new and distinct *Hosta* plant named 'Tears in Heaven' with an arching, rounded-mound habit of dense, cordate foliage of heavy glaucous bluish-colored above and whitish-blue below, retaining the glaucous covering until the end of summer. Long lanceolate leaves with sharply pointed apices and tapered base have intensely undulate margins and the lateral edges are folded upwardly veins with moderate dimpling between the veins and sinuate margins. The plant has pale lavender outer tepals with the tepals inside distinctly striped in the middle of the tepals with a darker lavender and white on the margins. The new plant is attractive and useful in landscaping as a specimen, in mass, or as a containerized plant by itself or in combination with other plants.

2 Drawing Sheets

Latin name and variety denomination of the plant:
Botanical classification: *Hosta* hybrid (Tratt.).
Variety denomination: 'Tears in Heaven'.

STATEMENT REGARDING PRIOR DISCLOSURES UNDER 37 CFR 1.77(B)(6)

*Hosta* 'Tears in Heaven' was first introduced by the inventor as a non-enabling description through the International Cultivar Registration Authority registration in early 2020. No plants of *Hosta* 'Tears in Heaven' have been sold, in this country or anywhere in the world, nor has any disclosure of the new plant been made, more than one year prior to the filing date of this application.

BACKGROUND AND ORIGIN OF THE PLANT

The present invention relates to a new and distinct *Hosta* plant, *Hosta* 'Tears in Heaven' hereinafter also referred to as the new plant or the cultivar name, 'Tears in Heaven'. *Hosta* 'Tears in Heaven' was hybridized at a wholesale nursery in Zeeland, Mich., USA in the Aug. 14, 2014 as a cross between two unreleased proprietary hybrids known as 11-355-2 (not patented) and H10-174 (not patented) as the female and male parents, respectively. The new plant is the selection of as a single seedling among several in that cross identified as 14-218-1 through the trial process. The new plant has been asexually propagated by division at the same nursery in Zeeland, Mich., USA since 2014, and also by careful plant shoot-tip tissue culture, with the resultant asexually propagated plants having retained all the same traits as the original plant.

BRIEF SUMMARY OF THE PLANT

There are over 7,000 registered *Hosta* cultivars with The American *Hosta* Society, which is the International Cultivar Registration Authority for the genus *Hosta* along with a similar number of unregistered cultivars. The nearest comparison cultivars known to the inventor are: 'Azure Snow' (not patented), 'Joy Ride' (not patented), 'Diamond Lake' U.S. Plant Pat. No. 30,769, 'Neptune' U.S. Plant Pat. No. 19,674, 'Queen of the Seas' (not patented), 'Voices in the Wind' copending U.S. Plant Patent Application. 'Winfield Blue' (not patented) and 'Waterslide' (U.S. Plant patent application Ser. No. 30,303).

'Azure Snow' has more cordate and broader foliage with less glaucous without a wavy margin, and the habit is flatter. 'Joy Ride' has a flatter habit and the leaves are not as bluish-green. 'Diamond Lake' has foliage that is more bullate, cordate with a broader, more rounded leaf with a less pointed apex. 'Neptune' is smaller in habit and leaf size, the leaves are narrower, have a more narrowly acute apex, with less wavy margins. 'Queen of the Seas' is more upright in habit with broader foliage having less glaucous blue foliage and less wavy margins. 'Voices in the Wind' has variegated foliage that is more cupped or folded. 'Winfield Blue' has shorter, more cordate foliage with less wavy margin and less folded and the apices are not as sharp. 'Waterslide' is smaller in leaf size and habit with more narrow folded foliage.

The female parent, 11-355-2, has a larger habit with less glaucous foliage with ruffled sinuate leaf margin, but without the upward folding. The male parent, H10-174 is smaller in habit and foliage with longer and wider, intense glaucous blue foliage with less wavy margins and without the upward folding.

Other *Hosta* cultivars have glaucous foliage, but 'Tears in Heaven' is distinct from the above listed *Hostas* and all other cultivars known to the discoverer by the following combined traits:

1. Arching, rounded-mound plant with dense foliage;
2. Lanceolate foliage with lateral edges folded upwardly and undulate margins, sharply pointed apices and tapered base;
3. Leaves with heavy glaucous bluish coloring above and glaucous whitish-blue below retained until the end of the summer;
4. Leaves have smooth top veins;
5. Tightly-compact pale lavender flowers on arching glaucous bluish-colored scapes above foliage.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
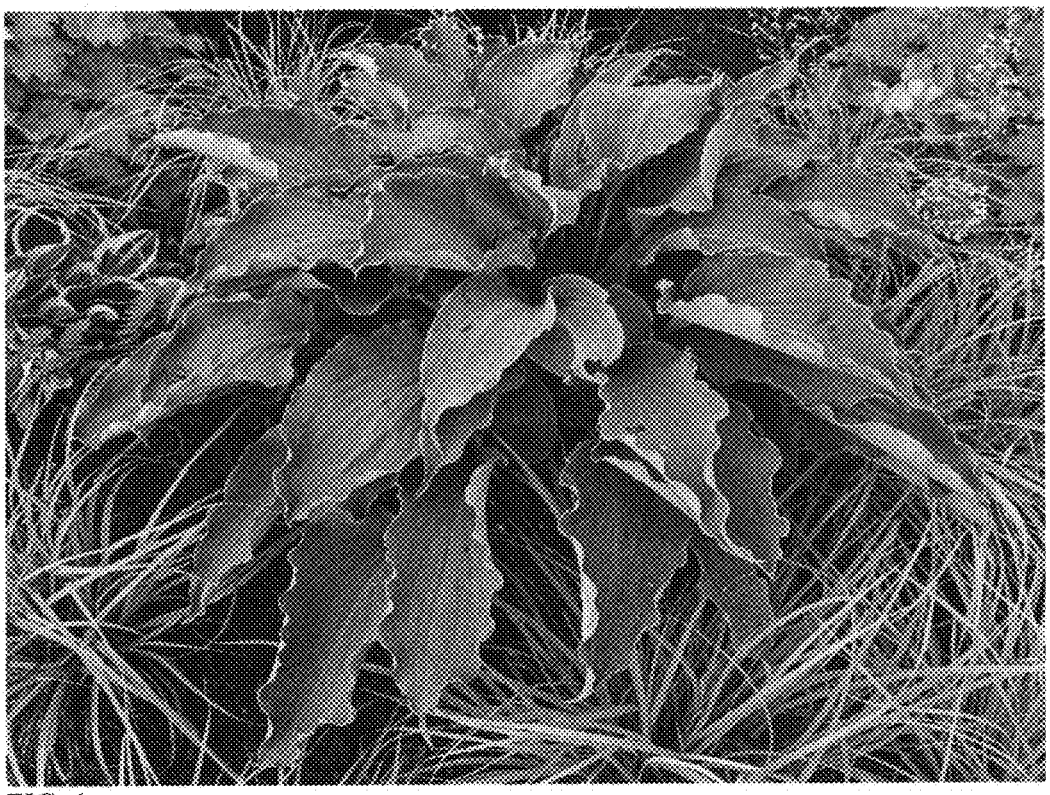
FIG. 1 shows a top view of a six-year-old plant showing plant habit.
Figure 2:
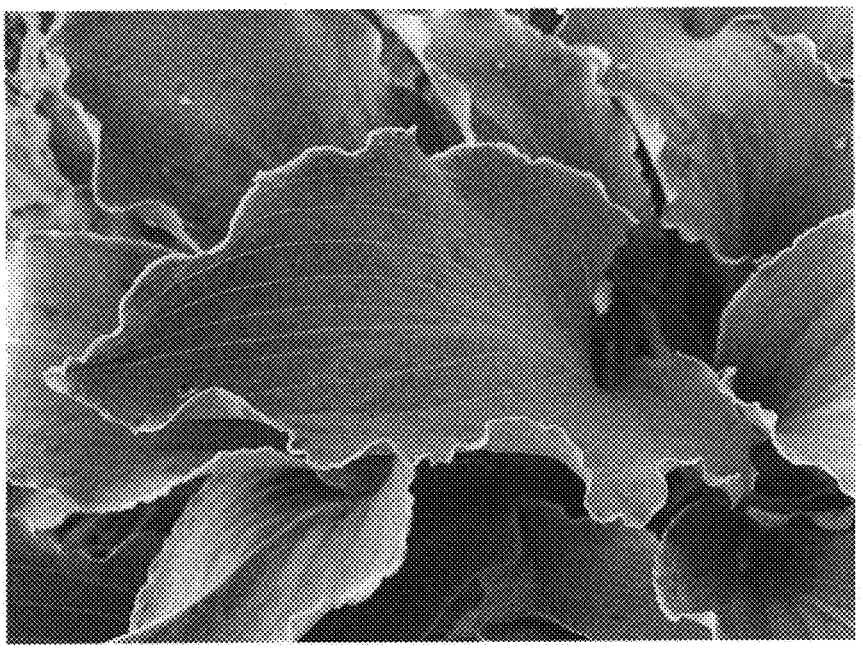
FIG. 2 shows a leaf demonstrating slightly folded undulate margins, and smooth surface.
Figure 3:
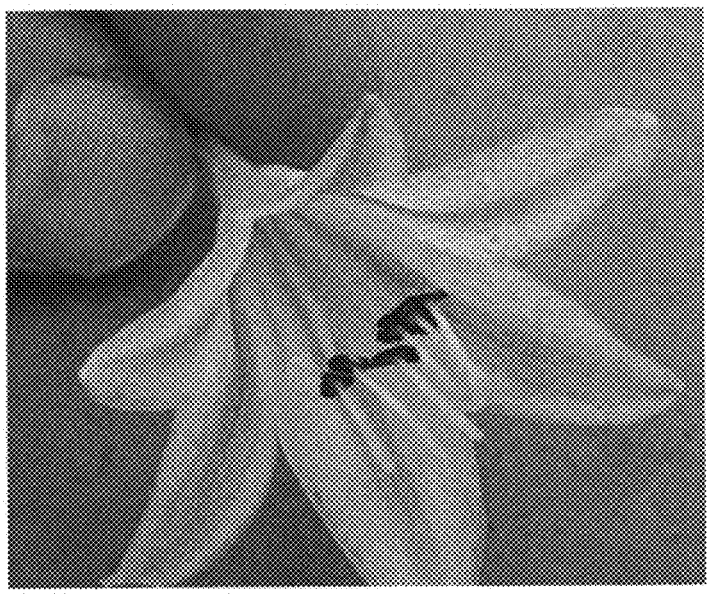
FIG. 3 shows a close-up of the inside of the flower.

The following descriptions and color references are based on the 2015 edition of The Royal Horticultural Society Colour Chart except where common dictionary terms are used. The new plant, *Hosta* 'Tears in Heaven', has not been observed under all possible environments. The phenotype may vary slightly with different environmental conditions, such as temperature, light, fertility, moisture and maturity levels, but without any change in the genotype. The following observations and size descriptions are of a six-year-old plant in a partially shaded trial garden in Zeeland, Mich. with supplemental water and fertilizer.

Botanical classification: *Hosta* x hybrid;

Parentage: Hybrid 11-355-2 comprising 'Joy Ride' (not patented), 'Neptune' and 'Fulda' (not patented) as the female parent, and H10-174 comprising 'Neptune' and 'Winfield Blue' (not patented) as the male parent;

Propagation: Garden division and sterile shoot-tip tissue culture;

Time to initiate roots from tissue culture: About two to three weeks;

Growth rate: Rapid;

Crop time: About 10 to 12 weeks to finish during the summer in a one-liter container from rooted tissue culture plantlet;

Rooting habit: Normal, fleshy, lightly branching; color nearest RHS NN155B depending on soil type;

Plant shape and habit: Hardy herbaceous perennial with basal rosette of leaves emerging from rhizomes producing a medium, symmetrical upright, low, rounded-mound of leaves;

Plant size: Foliage height about 38.1 cm above soil line to the top of the leaves and about 71.1 cm wide at the widest point just above the soil line;

Foliage description: Lanceolate; glabrous, heavily glaucous abaxial and adaxial; with acute to apiculate apex and cuneate base; margin entire and sinuate; with smooth surfaces; blades folded upward on edges, without twisting;

Leaf blade size: To about 20.3 cm long, 11.4 cm wide near base; average about 18.5 cm long, 10.5 cm wide;

Leaf blade color: Early season and shortly after emerging adaxial nearest RHS 137A with wax removed and between RHS N138A and RHS 188A with wax, abaxial nearest RHS 137B with wax removed and between RHS 190A and N138C with wax; mid-season adaxial nearest RHS 137A without wax and between RHS 122B and RHS 188B with wax, abaxial nearest RHS 137B with wax removed and between RHS 188C and RHS 122B with wax; late-season adaxial nearest RHS 137A with wax removed and between RHS N138B and RHS 188A with wax, abaxial nearest RHS 138A with wax removed and between RHS N138C and RHS 190A with wax;

Petiole: Entire, glabrous, glabrous, concavo-convex; mostly outwardly and straight from base of plant to leaf base with little bending or curving, strong but flexible; to about 26.0 cm long, 11.0 mm wide at base and 5.0 mm deep at base;

Petiole color: Adaxial distally without wax nearest RHS 137A and nearest a blend of RHS N138C and RHS 189B with wax, adaxial proximally nearest RHS 146B with wax and heavily maculate with between RHS N187B and RHS N186C; abaxial center without wax nearest RHS 145C, margin nearest RHS 137B and with wax nearest RHS 145C in center and margin between RHS N138C and RHS 190B with wax, with heavy maculate to nearly solid proximally of between RHS N187B and RHS N186C;

Veins: Parallel, smooth and flush with adaxial surface, abaxial slightly costate and smooth; typically 9 to 10 pairs and one midrib;

Veins color: Adaxial between RHS N138B and RHS 188B becoming nearest RHS 146D late in the season; abaxial between RHS 188C and RHS 122B with midrib proximally nearest RHS 145C and distally between 188C and RHS 122B;

Flower description:

Buds one day prior to opening: Clavate with acute apex and narrow tubular base; entire bud about 45.0 mm long, with swollen distal portion about 12.0 mm diameter and about 29.0 mm long, base tube about 16.0 mm long and about 3.5 mm diameter; buds slightly smaller distally;

Bud color: Base tube nearest RHS N82D; apical swollen portion nearest RHS N82C;

Flowers: Perfect; single; actinomorphic; funnelform; held slightly drooping to outwardly; about 42.0 mm wide and 59.0 mm long; fused in basal 33.0 mm; corolla to about 57.0 mm long and 46.0 mm wide at apex, tube portion about 18.0 mm long and 3.5 mm diameter (distal flowers smaller); persists for a normal period, usually one day on plant or as cut flower; scapes remain effective with flowers beginning late August for about five weeks in Michigan; about 50 flowers per scape;

Floral bracts: Subtending individual flowers; lanceolate; concavo-convex; acute apex; truncate clasping base; glaucous adaxial and abaxial; to about 54.0 mm long and 13.0 mm wide, decreasing distally;

Floral bract color: Adaxial blend nearest RHS 138C with moderate blushing along edges of nearest RHS N77C; abaxial between RHS 138C and RHS 194B with heavy blushing distally and along edges of nearest RHS N77C;

Flower fragrance: None detected;

Tepal: Six; typically two sets of three, glabrous, entire; oblanceolate with acute apex and fused base; inner set about 59.0 mm long and about 13.0 mm wide about 5.0 mm above fusion; outer set about 59.0 mm long and 12.0 mm wide about 5.0 mm above fusion;

Tepal color: Adaxial inner set margins nearest RHS NN155D and center stripe about 3.5 mm wide between RHS N80D and RHS N82D with clear margins in the distal portion and corolla tube nearest RHS NN155D in basal 8.0 mm, abaxial nearest RHS 84D including corolla tube; adaxial outer set margins nearest RHS NN155D and center stripe about 5.0 mm wide between RHS N80D and RHS N82D and corolla tube basal 8.0 mm nearest RHS NN155D, abaxial nearest RHS 84D including corolla tube;

Gynoecium: Single; tri-carpelled; 62.0 mm long; exserted;

*Style*.—Single; terete; approximately 56.0 mm long, 1.0 mm diameter, arcuate upward about 90 degrees in distal 10.0 mm; color base nearest RHS 2D, distally nearest 155A.

*Stigma*.—Globose, micro-puberulent; about 1.2 mm in across and 1.0 mm tall; color nearest RHS 155A.

*Ovary*.—Ellipsoidal; slightly sulcate longitudinally; about 5.0 mm long and 2.0 mm diameter at widest; rounded apex and truncate base; color nearest RHS N144D.

Androecium:

*Filaments*.—Typically six; terete; approximately 57.0 mm long and 0.8 mm in diameter; arcuate upward about 120 degrees in the apical 10.0 mm; color base nearest RHS 2D, nearest RHS 155A distally.

*Anthers*.—Elliptic; dorsifixed, longitudinally dehiscent; about 6.0 mm long and 2.5 mm wide; color nearest RHS N186B.

*Pollen*.—Abundant; elliptic, less than 0.1 mm long; color nearest RHS 17A.

Peduncle: Terete; usually one per mature division and ten per plant; glaucous, glabrous; slightly outwardly; to about 65.0 cm long, and about 8.0 mm in diameter at base; average about 62.0 cm and 7.5 mm diameter, flowering portion about 24.0 cm long;

Peduncle color: When flowering nearest RHS 138D;

Pedicel: Glabrous; glaucous; terete; secund, slightly curved downwardly; approximately 8.0 mm long and 2.0 mm diameter, decreasing in size distally;

Pedicel color: Distal portion nearest RHS 84D, proximally nearest RHS 138D;

Fruit: Oblong ellipsoid, with apiculate apex; tri-valved dehiscent capsule; about 35.0 cm long and 7.0 mm diameter; color when mature nearest RHS 161C;

Seed: Typically about 30 seeds per capsule; endospermic; flattened-elliptic wing surrounding embryo situated toward one end of ellipse; about 8.0 mm long and 3.0 mm wide and 1.5 thick; color nearest RHS 202A;

Disease tolerance and resistance: The new plant has not shown any resistance to pests and diseases common to *Hostas*.

Growth conditions: The new plant grows best and shows best coloration with plenty of moisture, adequate drainage and light shade, but is able to tolerate some drought when mature, and tolerates direct sun without leaf burn, especially during the cooler parts of the day and when provided sufficient water. Hardiness at least from USDA zone 3 through 9, and other disease resistance is typical of that of other *Hostas*.

It is claimed:

1. A new and distinct ornamental plant cultivar named *Hosta* 'Tears in Heaven' as herein described and illustrated.

* * * * *